United States Patent [19]

Curzons

[11] Patent Number: 4,639,534
[45] Date of Patent: Jan. 27, 1987

[54] ISOLATION OF PSEUDOMONIC ACID

[75] Inventor: Alan D. Curzons, Brighton, England

[73] Assignee: Beecham Group p.l.c., England

[21] Appl. No.: 684,479

[22] Filed: Dec. 21, 1984

Related U.S. Application Data

[60] Continuation of Ser. No. 332,669, Dec. 21, 1981, abandoned, which is a continuation of Ser. No. 207,773, Nov. 17, 1980, abandoned, which is a division of Ser. No. 36,061, May 4, 1979, abandoned.

[30] Foreign Application Priority Data

May 20, 1978 [GB] United Kingdom ............... 20958/78

[51] Int. Cl.$^4$ .......................................... C07D 309/10
[52] U.S. Cl. ..................................................... 549/414
[58] Field of Search ........................................ 549/414

[56] References Cited

U.S. PATENT DOCUMENTS 4,071,536  1/1978  Barrow et al. ...................... 549/414

FOREIGN PATENT DOCUMENTS 1395907  5/1975  United Kingdom .

Primary Examiner—Nicky Chan
Attorney, Agent, or Firm—Jacobs & Jacobs

[57] ABSTRACT

Procedure for isolating lithium pseudomonate from a crude preparation containing pseudomonic acid by extracting the crude preparation into a suitable organic solvent in which pseudomonic acid is soluble, treating the extract with a lithium alkanoic acid and separating the resulting crystalline non-hygroscopic lithium pseudomonate, the crude preparation containing pseudomonic acid being a culture medium on or in which pseudomonic acid producing strains of bacteria have been grown, such as *Pseudomonas fluorescens*.

4 Claims, No Drawings

ISOLATION OF PSEUDOMONIC ACID

This application is a continuation of application Ser. No. 332,669 filed Dec. 21, 1981, which is a continuation of Ser. No. 207,773 filed Nov. 17, 1980, which in turn is a division of application Ser. No. 036,061 filed May 4, 1979, all now abandoned.

This invention relates to a novel salt of an antibacterial compound and to a process for its preparation Psuedomonic acid is the compound of formula (I):

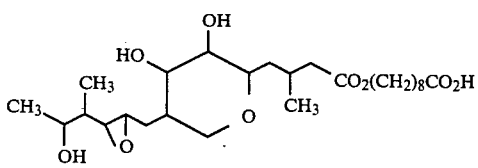

This compound is disclosed in British Pat. No. 1,395,907 as having antibacterial activity and it is therefore of value in the treatment of bacterial infections in man and animals. The method described in British Pat. No. 1,395,907 for the preparation of pseudomonic acid comprises isolating a mixture containing the principle active acid components from a culture medium on or in which *Pseudomonas fluorescens* has been grown under aerobic conditions and thereafter separating the acid from the mixture by chromatography.

It has now been found that pseudomonic acid can be isolated directly from an extracted solution of the fermentation broth, in the form of its lithium salt.

The lithium salt of pseudomonic acid (referred to herein as lithium pseudomonate) is a novel compound and forms one aspect of the present invention. Although British Pat. No. 1,395,907 discloses the sodium salt of pseudomonic acid, it does not disclose or foreshadow the use of the lithium salt. Whereas the sodium salt is an amorphous and hydroscopic compound, surprisingly lithium pseudomonate is stable, crystalline and non-hygroscopic. In addition, the lithium salt is very much less soluble than the sodium salt. These properties could not have been predicted from British Pat. No. 1,395,907 and make lithium pseudomonate a useful intermediate in the isolation or purification of pseudomonic acid.

Accordingly, in a second aspect the present invention provides a process for isolation of lithium pseudomonate from a crude preparation containing pseudomonic acid, which process comprises extracting the crude preparation into a polar, organic, water-immiscible solvent in which pseudomonic acid is soluble, treating the extract with a lithium salt which is at least slightly soluble in the water-immiscible solvent, and separating the resulting lithium pseudomonate.

The lithium pseudomonate may then be converted into the free acid, pseudomonic acid, or a different salt thereof, by conventional techniques.

The process of this invention is particularly suitable for isolating pseudomonic acid, in the form of its lithium salt, from culture media on or in which pseudomonic acid producing strains of bacteria have been grown. In such a case, the process is most suitably carried out as follows.

A pseudomonic acid producing bacterium, in general a strain of bacterium of the family Pseudomonas, is cultured by a standard method under aerobic conditions in or on a suitable culture medium. Such culture media are generally known, and contain inorganic salts and sources of assimilable nitrogen and carbon. Most suitably the bacterium used is *Pseudomonas fluorescens*. One suitable publicly available strain is *Pseudomonas fluorescens* NCIB 10586. The microorganism is allowed to grow until a suitable quantity of pseudomonic acid is present in the culture medium. Solid particles may then be removed from the medium by filtration or centrifugation to produce a clear liquor. The pH of the clear liquor is adjusted to pH 3.0–5.0, suitably about pH 4.5.

This acidified aqueous solution is then extracted into a polar, organic, water-immiscible solvent. Aprotic solvents are preferred. The solvent should have sufficient polarity to adequately dissolve the pseudomonic acid. Suitable solvents include ethyl acetate, butanol, methyl isobutyl ketone (MIBK) and methylene dichloride. Alternatively, mixed solvents may be employed such as ether containing about 5% ethanol. A preferred solvent is MIBK.

The volume of solvent used for the extraction should be kept to a minimum whilst ensuring a good physical separation between the two phases. When extracting a culture liquor a suitable volume is ½ to 1/6, preferably ¼ of the volume of the liquor to be extracted.

It is often advantageous to wash the extract with brine, for example using a volume of 1/10 that of the extract, in order to reduce the water content of the extract.

The next step of the process is to treat the extract with a lithium salt. The lithium salt employed should ideally be more soluble in the solvent than lithium pseudomonate. It is preferably the lithium salt of an organic carboxylic acid, for example a salt of an alkanoic acid of formula (II):

$$R-CO_2^-Li^+ \qquad (II)$$

wherein R is an alkyl group, containing for example from 1 to 20 carbon atoms, preferably from 1 to 8 carbon atoms.

Examples of suitable lithium salts include the acetate, propionate, or hexanoate, a preferred salt being lithium 2-ethylhexanoate.

The lithium salt may be added to the extract in solid form, but it is preferable to add it as a concentrated solution in a co-solvent which dissolves the lithium salt but which does not substantially solubilise lithium pseudomonate. Such co-solvents include ethanol and, preferably, methanol.

In general it is preferred to use approximately a 10% excess of lithium salt and to add a solution of the salt slowly to the extract. In most cases, the lithium pseudomonate will crystallise out, a process which is facilitated by cooling to about 0°–5° C. The lithium pseudomonate may be separated by conventional techniques. It may be advantageous, after separating a first crop of lithium pseudomonate, to concentrate and separate a second crop.

Because lithium pseudomonate is not hygroscopic, it can be dried in an air oven. This is not possible with sodium pseudomonate, or even with pseudomonic acid itself which is difficult to dry in other than a vacuum oven, or very carefully at low temperature.

The lithium pseudomonate can be converted into other salts or the free acid itself by conventional techniques, for example by acidification and extraction into organic solvent.

The invention is illustrated with reference to the following Examples.

EXAMPLE 1

Isolation of Lithium Pseudomonate

A culture medium containing pseudomonic acid was acidified to pH 4.5 using 20% hydrochloric acid and extracted with ¼ of its volume of methyl isobutyl ketone (MIBK). The MIBK extract was washed with 1/10 of its volume of saturated brine. The pseudomonic acid content at this stage was 2,500 µg/ml, and the water content was 1.0%.

To 10 l of the MIBK extract was added dropwise a solution of 9.0 g of lithium ethyl hexanoate in 35 ml methanol over a period of 0.5 hours at ambient temperature and the mixture was stirred for a further one hour at 20° C. and then one hour at 5° C. The precipitated product was isolated by filtration, washed with MIBK and air dried at 50° C. to give lithium pseudomonate, mp 169° C., yield 26.5 g (90%), purity 87%.

EXAMPLE 2

Conversion of Pseudomonic Acid 10 g of lithium pseudomonate from Example 1 were dissolved in 200 ml of water. MIBK (85 ml) was added and the pH adjusted to 4.0 with 4N hydrochloric acid. The upper MIBK layer was separated, dried over anhydrous sodium sulphate, and the free acid was precipitated by the addition of 130 ml of heptane. After cooling to 5° C., pseudomonic acid was isolated by filtration. Mp 77°–78° C., yield 8.0 g (85%), purity 90%.

I claim:

1. A process for the isolation of pseudomonic acid from a crude preparation thereof which process comprises extracting the crude preparation into a polar, organic, water-immiscible solvent in which the pseudomonic acid is soluble, treating the extract with a lithium salt of an alkanoic acid of formula $R-CO_2^-Li^+$, wherein R is an alkyl group containing from 1 to 20 carbon atoms, separating the resulting lithium pseudomonate and thereafter hydrolysing the lithium pseudomonate to produce pseudomonic acid.

2. A process as claimed in claim 1 wherein the crude preparation containing pseudomonic acid is a culture medium on or in which pseudomonic acid producing strains of bacteria have been grown.

3. A process as claimed in claim 2 wherein the bacteria is *Pseudomonas fluorescens*.

4. A process as claimed in claim 1 wherein the lithium salt is lithium 2-ethylhexanoate.

* * * * *